(12) United States Patent
Iwasaki et al.

(10) Patent No.: US 9,618,457 B2
(45) Date of Patent: Apr. 11, 2017

(54) CHEMICAL SENSOR, CHEMICAL SENSOR MODULE, CHEMICAL DETECTION APPARATUS, AND CHEMICAL DETECTION METHOD

(71) Applicant: Sony Corporation, Tokyo (JP)

(72) Inventors: Masanori Iwasaki, Kanagawa (JP); Nobuyuki Matsuzawa, Tokyo (JP); Kensaku Maeda, Kanagawa (JP); Yusuke Moriya, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 290 days.

(21) Appl. No.: 14/356,730

(22) PCT Filed: Oct. 26, 2012

(86) PCT No.: PCT/JP2012/006884
§ 371 (c)(1),
(2) Date: May 7, 2014

(87) PCT Pub. No.: WO2013/080432
PCT Pub. Date: Jun. 6, 2013

(65) Prior Publication Data
US 2014/0299750 A1    Oct. 9, 2014

(30) Foreign Application Priority Data

Nov. 28, 2011 (JP) ................. 2011-259452

(51) Int. Cl.
*G01N 21/84*    (2006.01)
*G02B 6/34*    (2006.01)
*G01N 21/64*    (2006.01)

(52) U.S. Cl.
CPC .......... *G01N 21/84* (2013.01); *G01N 21/643* (2013.01); *G01N 21/648* (2013.01); *G01N 21/6454* (2013.01); *G02B 6/34* (2013.01)

(58) Field of Classification Search
CPC ....................................................... G02B 6/34
See application file for complete search history.

(56) References Cited

U.S. PATENT DOCUMENTS

| | | | |
|---|---|---|---|
| 6,287,871 B1* | 9/2001 | Herron | G01N 21/6452 422/82.08 |
| 7,384,797 B1* | 6/2008 | Blair | G01N 21/6452 385/12 |

(Continued)

*Primary Examiner* — Kara E Geisel
*Assistant Examiner* — Dominic J Bologna
(74) *Attorney, Agent, or Firm* — Chip Law Group

(57) ABSTRACT

A chemical sensor according to an embodiment of the present technology includes a substrate, a low refractive index layer, a high refractive index layer, and a light detection unit. The low refractive index layer is laminated on the substrate and has a second refractive index smaller than a first refractive index that is a refractive index of a detection target object. The high refractive index layer is laminated on the low refractive index layer, has a third refractive index larger than the first refractive index, and includes a holding surface on which the detection target object is held, and illumination light propagates therein. The light detection unit is provided on the substrate and detects detection target light generated from the detection target object by the illumination light.

15 Claims, 24 Drawing Sheets

(56) References Cited

U.S. PATENT DOCUMENTS

| | | | | |
|---|---|---|---|---|
| 8,569,716 B2* | 10/2013 | Sonnleitner | ........ | G01N 21/6454 |
| | | | | 250/458.1 |
| 2006/0051244 A1* | 3/2006 | Lehmann | ........... | G01N 21/6428 |
| | | | | 422/82.11 |
| 2009/0156415 A1* | 6/2009 | Remacle | .............. | C12Q 1/6837 |
| | | | | 506/9 |
| 2010/0308233 A1* | 12/2010 | Sonnleitner | .......... | G01N 21/648 |
| | | | | 250/458.1 |
| 2011/0306039 A1* | 12/2011 | Chiou | ................... | G01J 1/0425 |
| | | | | 435/6.1 |

* cited by examiner

| Refractive index n3 | Refractive index n1, n2 | | | | | | | | | | | | | |
|---|---|---|---|---|---|---|---|---|---|---|---|---|---|---|
| | | 1.1 | 1.125 | 1.15 | 1.175 | 1.2 | 1.225 | 1.25 | 1.275 | 1.3 | 1.325 | 1.35 | 1.375 | 1.4 | 1.425 |
| 1.8 | 37.7 | 38.7 | 39.7 | 40.8 | 41.8 | 42.9 | 44.0 | 45.1 | 46.2 | 47.4 | 48.6 | 49.8 | 51.1 | 52.3 |
| 1.825 | 37.1 | 38.1 | 39.1 | 40.1 | 41.1 | 42.2 | 43.2 | 44.3 | 45.4 | 46.6 | 47.7 | 48.9 | 50.1 | 51.3 |
| 1.85 | 36.5 | 37.5 | 38.4 | 39.4 | 40.4 | 41.5 | 42.5 | 43.6 | 44.6 | 45.7 | 46.9 | 48.0 | 49.2 | 50.4 |
| 1.875 | 35.9 | 36.9 | 37.8 | 38.8 | 39.8 | 40.8 | 41.8 | 42.8 | 43.9 | 45.0 | 46.1 | 47.2 | 48.3 | 49.5 |
| 1.9 | 35.4 | 36.3 | 37.2 | 38.2 | 39.2 | 40.1 | 41.1 | 42.1 | 43.2 | 44.2 | 45.3 | 46.4 | 47.5 | 48.6 |
| 1.925 | 34.8 | 35.8 | 36.7 | 37.6 | 38.6 | 39.5 | 40.5 | 41.5 | 42.5 | 43.5 | 44.5 | 45.6 | 46.7 | 47.8 |
| 1.95 | 34.3 | 35.2 | 36.1 | 37.1 | 38.0 | 38.9 | 39.9 | 40.8 | 41.8 | 42.8 | 43.8 | 44.8 | 45.9 | 47.0 |
| 1.975 | 33.8 | 34.7 | 35.6 | 36.5 | 37.4 | 38.3 | 39.3 | 40.2 | 41.2 | 42.1 | 43.1 | 44.1 | 45.1 | 46.2 |
| 2.0 | 33.4 | 34.2 | 35.1 | 36.0 | 36.9 | 37.8 | 38.7 | 39.6 | 40.5 | 41.5 | 42.5 | 43.4 | 44.4 | 45.4 |

| n-th total reflection | 1 | 2 | 3 | 4 |
|---|---|---|---|---|
| Ratio of opening size [%] | 50.0 | 57.7 | 70.7 | 100 |
| Opening ratio [%] | 25.0 | 33.3 | 50.0 | 100 |
| Amount of light emitted from each opening | 0.25 | 0.25 | 0.25 | 0.25 |
| Sum of amounts of light lost from opening | 0.25 | 0.50 | 0.75 | 1.00 |

FIG.15

| n-th total reflection | 1 | 2 | 3 | 4 |
|---|---|---|---|---|
| Ratio of opening size [%] | 48.6 | 55.6 | 66.9 | 90.0 |
| Opening ratio [%] | 23.6 | 30.9 | 44.7 | 81.0 |
| Amount of light emitted from each opening | 0.24 | 0.24 | 0.24 | 0.24 |
| Sum of amounts of light lost from opening | 0.24 | 0.47 | 0.71 | 0.94 |

FIG.16

| n-th total reflection | 1 | 2 | 3 | 4 | 5 | 6 | 7 | 8 |
|---|---|---|---|---|---|---|---|---|
| Ratio of opening size [%] | 35.0 | 37.4 | 40.3 | 44.0 | 49.0 | 56.2 | 68.0 | 92.7 |
| Opening area [%] | 12.3 | 14.0 | 16.2 | 19.4 | 24.0 | 31.6 | 46.2 | 86.0 |
| Total number of times of total reflection 8 | 0.12 | 0.12 | 0.12 | 0.12 | 0.12 | 0.12 | 0.12 | 0.12 |
| Amount of light emitted from each opening | 0.12 | 0.12 | 0.12 | 0.12 | 0.12 | 0.12 | 0.12 | 0.12 |
| Sum of amounts of light lost from opening | 0.12 | 0.25 | 0.37 | 0.49 | 0.61 | 0.74 | 0.86 | 0.98 |

CHEMICAL SENSOR, CHEMICAL SENSOR MODULE, CHEMICAL DETECTION APPARATUS, AND CHEMICAL DETECTION METHOD

TECHNICAL FIELD

The present technology relates to a chemical sensor, a chemical sensor module, a chemical detection apparatus, and a chemical detection method for detecting chemicals using light emission due to a chemical bond.

BACKGROUND ART

A chemical sensor that detects chemicals using light emission due to a chemical bond has been studied. Specifically, if a probe material specifically bonding to a target material to be detected is adhered to the sensor and a sample is supplied to the sensor, a target material included in the sample bonds to the probe material. For example, by using a fluorescent label that can be introduced into a composite material of a target material and a probe material to cause the composite material to emit light, it is possible to detect the emitted light by a photoelectric conversion element. By causing a plurality of types of probe materials to be adhered to the sensor, it is also possible to specify the type of the target material included in the sample.

In such a chemical sensor, in order to perform the detection with high sensitivity and high accuracy, it is necessary to introduce only emitted light generated due to the bond between the target material and the probe material into the photoelectric conversion element and to eliminate light other than that, e.g., excitation light for generating fluorescent light.

For example, Patent Document 1 discloses a "biosensor with evanescent waveguide and integrated sensor" that uses an evanescent wave (near-field light) of excitation light to cause a sample to emit fluorescent light, similarly. The sensor has a configuration in which a filter, a contact cladding layer, and a waveguide layer are laminated in the stated order, and a sample is placed on the waveguide layer. It has a configuration in which excitation light (laser) is introduced into the waveguide layer in a direction parallel to the layer, and the detector detects the fluorescent light the fluorescent light from the sample that is excited with an evanescent wave leaked from the interface of the waveguide layer.

Moreover, Patent Document 2 discloses an "all polymer optical waveguide sensor" that uses an evanescent wave of excitation light to cause a sample to emit fluorescent light. The sensor has a configuration in which a polymer waveguide is formed on a polymer substrate, and a sample is fixed on the polymer substrate. The sample is excited with an evanescent wave of a light wave (coherent light) traveling through the polymer waveguide, and generates fluorescent light, which is detected by a detector.

In any of the inventions described in Patent Document 1 and Patent Document 2, the excitation light is confined in the waveguide structure to prevent the excitation light from reaching the photoelectric conversion element. Therefore, the evanescent wave for causing the sample fixed on the waveguide structure to emit fluorescent light is an element in both inventions.

CITATION LIST

Patent Document

Patent Document 1: Japanese Unexamined Patent Application Publication No. 2010-518389 (paragraphs [0023] and [0126])

Patent Document 2: Japanese Unexamined Patent Application Publication No. 2009-511896 (paragraphs [0056] and [0102])

DISCLOSURE OF THE INVENTION

Problem to be Solved by the Invention

However, because the intensity of the evanescent wave is much smaller than the intensity of light introduced into the waveguide structure, the inventions described above cannot use optical energy efficiently. Furthermore, because the thickness of the waveguide structure is limited (to several ten nm) to use the evanescent wave in the optimal conditions, the manufacture of the sensor is considered to be difficult or to cost a lot. Furthermore, because the travel distance of the evanescent wave is very small (about several ten nm), if a fluorescent material is not present in the vicinity of the surface of the sample (within the travel distance of the evanescent wave), it cannot be detected.

In view of the circumstances as described above, it is an object of the present technology to provide a chemical sensor, a chemical sensor module, a chemical detection apparatus, and a chemical detection method that are capable of detecting chemicals with high accuracy and high sensitivity.

Means for Solving the Problem

In order to achieve the above-mentioned object, a chemical sensor according to an embodiment of the present technology includes a substrate, a low refractive index layer, a high refractive index layer, and a light detection unit.

The low refractive index layer is laminated on the substrate and has a second refractive index smaller than a first refractive index that is a refractive index of a detection target object.

The high refractive index layer is laminated on the low refractive index layer, has a third refractive index larger than the first refractive index, and includes a holding surface on which the detection target object is held, and illumination light propagates therein.

The light detection unit is provided on the substrate and detects detection target light generated from the detection target object by the illumination light.

According to this configuration, the illumination light introduced into the high refractive index layer is refracted and transmitted to the detection target object, and the first refractive index being a refractive index of the detection target object is larger than the second refractive index being a refractive index of the low refractive index layer as described above. Therefore, by causing the illumination light to enter the high refractive index layer at an appropriate incidence angle, it is possible to cause the illumination light to be refracted and transmitted to the detection target object while causing the illumination light to be totally reflected on the interface of the high refractive index layer and the low refractive index layer. Therefore, it is possible to detect the detection target light generated from the detection target object by the light detection unit while preventing the illumination light from reaching the light detection unit located below the low refractive index layer. Therefore, it is possible to prevent the detection accuracy of the illumination light by the light detection unit from lowering.

The holding surface may further have adsorption regions to which the detection target object is adsorbed and non-adsorption regions to which the detection target object is not adsorbed.

According to this configuration, because the non-adsorption region is not in contact with the detection target object that causes the illumination light to be refracted and transmitted thereto, it is possible to prevent the refraction and transmission of the illumination light in the non-adsorption region from occurring. That is, in the case where the non-adsorption region faces air or is in contact with at least a material having a refractive index sufficiently smaller than a refractive index of the detection target object (first refractive index), the illumination light may be totally reflected in the non-adsorption region. Accordingly, because the illumination light reaches the detection target object on the adsorption region but is totally reflected on the non-adsorption region, it is possible to prevent the optical energy from being lost.

The adsorption regions may be separated by the non-adsorption regions.

According to this configuration, because the adsorption regions can be disposed in an island shape, it is possible to detect various types of chemicals at the same time by causing different target materials to be adsorbed in the respective adsorption regions.

The light detection unit may include a plurality of light detection units, and the adsorption regions may be opposed to the light detection units, respectively.

According to this configuration, because the one-to-one relationship is established between the detection target object adsorbed to the respective adsorption regions and the light detection unit, it is possible to detect the detection target light with high accuracy.

The light detection unit may include a plurality of light detection units, and the respective adsorption regions may be opposed to the plurality of light detection units.

According to this configuration, because the detection target object adsorbed to the respective adsorption regions corresponds to the plurality of light detection units, it is possible to confirm the properties of light emission spectrum of the detection target light in one adsorption region.

The adsorption regions may be formed in such a way that an area thereof is increased along a direction in which the illumination light propagates.

According to this configuration, it is possible to cause a uniform amount of illumination light to enter the respective adsorption regions. As described above, because the illumination light is totally reflected on the non-adsorption region, the optical energy is not lost. However, in the adsorption area, it is lost by entering the detection target object. That is, in the adsorption area located at a long distance in the direction in which the illumination light propagates, the intensity of the illumination light per unit surface is small, as compared with the adsorption region located at a short distance. Here, as in this configuration, by gradually increasing the size of the adsorption region, it is possible to adjust the proportion of the amount of light entering the detection target object and the amount of light totally reflected, and to cause a uniform amount of illumination light to enter the respective adsorption region.

The adsorption regions may be formed by hydrophilic processing applied to the holding surface, and the non-adsorption regions may be formed by hydrophobic processing applied to the holding surface.

According to this configuration, the adsorption region and the non-adsorption region can be segmented in the case where the detection target object includes a hydrophilic material.

The adsorption regions may be formed by hydrophobic processing applied to the holding surface, and the non-adsorption regions may be formed by hydrophilic processing applied to the holding surface.

According to this configuration, the adsorption region and the non-adsorption region can be segmented in the case where the detection target object includes a hydrophobic material.

The non-adsorption regions may be covered by a coating film to which the detection target object is not adsorbed, and the adsorption regions do not have to be covered by the coating film.

According to this configuration, the adsorption region and the non-adsorption region can be segmented in the case where the detection target object includes a material that can be adsorbed to the holding surface.

The coating film may have light reflectivity.

According to this configuration, it is possible to reflect the illumination light by the coating film. This is particularly effective in the case where a material having a high refractive index is laminated on the non-adsorption region.

The above-mentioned chemical sensor may further include a color filter that is provided between the light detection unit and the low refractive index layer, and blocks wavelengths other than that of the detection target light.

According to this configuration, it is possible to secondarily prevent the illumination light from reaching the light detection unit. As described above, because the illumination light is totally reflected on the interface of the high refractive index layer and the low refractive index layer, it does not reach the light detection unit in principle. However, for example, the case where it reaches the light detection unit through the same path as that of the detection target light by being reflected on the detection target object is conceivable. Here, by removing such an illumination light component with a color filter, it is possible to detect the detection target light with higher accuracy.

The chemical sensor may further include an on-chip lens that is provided between the light detection unit and the low refractive index layer, and collects the detection target light on the light detection units.

According to this configuration, it is possible to collect the detection target light on the light detection unit by the on-chip lens, and thus to detect the detection target light with higher accuracy.

The chemical sensor may further include light blocking walls that are provided on the low refractive index layer and partition the low refractive index layer into areas opposed to the respective light detection units.

According to this configuration, it is possible to block the detection target light generated from an adjacent detection target object, and to prevent cross talk from occurring.

The illumination light may be excitation light, and the detection target light may be fluorescent light.

In order to achieve the above-mentioned object, a chemical sensor module according to an embodiment of the present technology includes a chemical sensor and a light introduction unit.

The chemical sensor includes a substrate, a low refractive index layer that is laminated on the substrate and has a second refractive index smaller than a first refractive index that is a refractive index of a detection target object, a high refractive index layer in which illumination light propagates, which is laminated on the low refractive index layer, has a third refractive index larger than the first refractive index, and includes a holding surface on which the detection target object is held, and a light detection unit that is provided on the substrate and detects detection target light generated from the detection target object by the illumination light.

The light introduction unit is joined to the chemical sensor and introduces the illumination light into the high refractive index layer.

In order to achieve the above-mentioned object, a chemical detection apparatus according to an embodiment of the present technology includes a chemical sensor module and a light source.

The chemical sensor module includes a chemical sensor including a substrate, a low refractive index layer that is laminated on the substrate and has a second refractive index smaller than a first refractive index that is a refractive index of a detection target object, a high refractive index layer in which illumination light propagates, which is laminated on the low refractive index layer, has a third refractive index larger than the first refractive index, and includes a holding surface on which the detection target object is held, and a light detection unit that is provided on the substrate and detects detection target light generated from the detection target object by the illumination light, and a light introduction unit that is joined to the chemical sensor and introduces the illumination light into the high refractive index layer.

The light source applies the illumination light to the light introduction unit.

In order to achieve the above-mentioned object, a chemical detection method according to an embodiment of the present technology includes preparing a chemical sensor including a substrate, a low refractive index layer that is laminated on the substrate and has a second refractive index smaller than a first refractive index that is a refractive index of a detection target object, a high refractive index layer in which illumination light propagates, which is laminated on the low refractive index layer, has a third refractive index larger than the first refractive index, and includes a holding surface on which the detection target object is held, and a light detection unit that is provided on the substrate and detects detection target light generated from the detection target object by the illumination light.

By a light introduction unit, the illumination light is introduced into the high refractive index layer.

By the light detection unit, the detection target light is detected.

Effect of the Invention

As described above, according to the present technology, it is possible to provide a chemical sensor, a chemical sensor module, and a chemical detection method that are capable of detecting chemicals with high accuracy and high sensitivity.

BRIEF DESCRIPTION OF DRAWINGS

FIG. 10 A table showing incidence angles of illumination light on the chemical sensor.

FIG. 15 A table showing the amount of the illumination light of the chemical sensor.

FIG. 16 A table showing the amount of the illumination light of the chemical sensor.

FIG. 17 A table showing the amount of the illumination light of the chemical sensor.

MODE(S) FOR CARRYING OUT THE INVENTION

First Embodiment

A chemical sensor according to a first embodiment of the present technology will be described.

[Configuration of Chemical Sensor]

Figure 1:
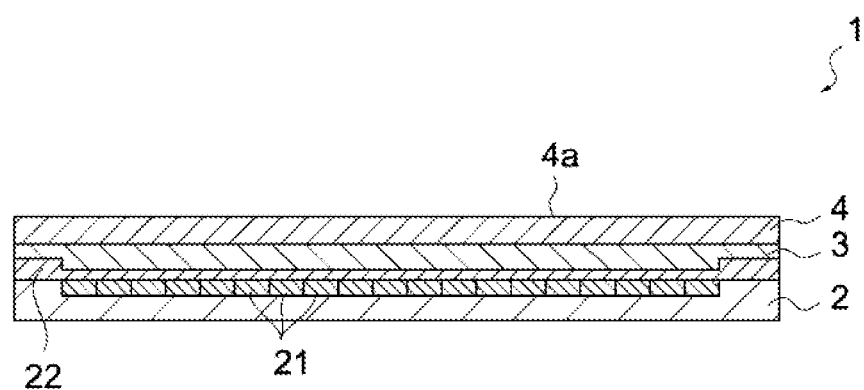
FIG. 1 A cross-sectional view showing a configuration of a chemical sensor according to a first embodiment.
Figure 2:
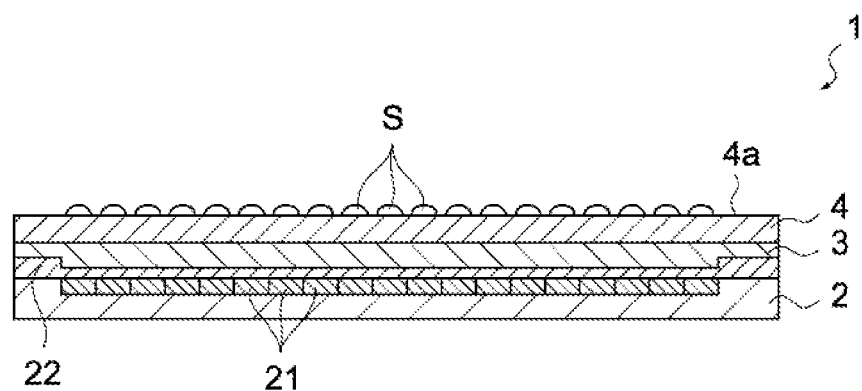
FIG. 2 A cross-sectional view showing a detection target object placed on the chemical sensor.

FIG. 1 is a cross-sectional view showing a configuration of a chemical sensor 1 according to the first embodiment. As shown in the figure, the chemical sensor 1 has a configuration in which a substrate 2, a low refractive index layer 3, and a high refractive index layer 4 are laminated in the stated order. Moreover, a detection target object covers the chemical sensor 1 when the chemical sensor 1 is used. FIG. 2 is a cross-sectional view showing detection target objects S placed on the chemical sensor 1.

In the following description, the refractive index (absolute refractive index, the same shall apply hereinafter) of the detection target object S is referred to as a first refractive index $n1$, the refractive index of the low refractive index layer 3 is referred to as a second refractive index $n2$, and the refractive index of the high refractive index layer 4 is referred to as a third refractive index $n3$. Although the details will be described later, these refractive indexes have a relationship of increasing in the order of the second refractive index n2, the first refractive index n1, and the third refractive index n3.

On the substrate 2, light detection units 21 are provided. The light detection unit 21 may each be an image sensor (CMOS, CCD, or the like) in which pixels (photoelectric conversion elements) are two-dimensionally arranged, and various sensors such as a line sensor in which pixels are one-dimensionally arranged and a photosensor using organic photoelectric conversion that are capable of detecting light can be used. On the substrate 2, a wiring or the like (not shown) that is connected to the light detection unit 21 may be provided. In FIG. 1 and FIG. 2, a protective insulating film 22 of the image sensor is provided on the substrate 2. However, it is not provided depending on the configuration of the light detection unit 21 in some cases.

The low refractive index layer 3 is a layer laminated on the substrate 2, and has the second refractive index n2 smaller than the first refractive index n1 (refractive index of the detection target objects S). That is, the low refractive index layer 3 can be formed of a material having a refractive index that is more than 1 (air) and less than the first refractive index (e.g., 1.5). In addition, as a material of the low refractive index layer 3, a material having at least high optical transparency in the wavelength range of light to be detected (hereinafter, referred to as detection target light) to be described later is favorable.

Examples of such a material include fluorine containing-hollow silica particle-containing polysiloxane resin (n=1.2 to 1.35 (depending on silica particle size)), fluorine-containing polysiloxane resin (n=1.42), fluorine-containing acrylic resin (n=1.42), and hollow silica particle-containing polysiloxane resin (n=1.2 to 1.35) depending on silica particle size)). It should be noted that the refractive index shown here is a refractive index with respect to an optical wavelength of 550 nm.

The thickness of the low refractive index layer 3 is favorably not less than 50 nm and not more than 1 mm, and is more favorably not less than 100 nm and not more than 1 µm, or not less than 50 µm and not more than 500 µm.

The high refractive index layer 4 is a layer laminated on the low refractive index layer 3, and has the third refractive index n3 larger than the first refractive index n1 (refractive index of the detection target object S). That is, the high refractive index layer 4 can be formed of a material having a refractive index higher than the first refractive index (e.g., 1.5). In addition, as a material of the high refractive index layer 4, a material having at least high optical transparency in the wavelength range of the detection target light is favorable. Furthermore, a material having high optical transparency in the wavelength range of light to be introduced into the high refractive index layer 4 (hereinafter, referred to as illumination light) to be described later is favorable.

Examples of such a material include silicon nitride (n=1.9), silicon nitride oxide (n=1.85), titanium oxide dispersion polysiloxane resin (n=1.8), and titanium oxide dispersion acrylic resin to which a thermosetting material is added (n=1.8). It should be noted that the refractive index shown here is a refractive index with respect to an optical wavelength of 550 nm.

The thickness of the high refractive index layer 4 is not particularly limited, but is favorably thin to prevent the detection target light from attenuating. The high refractive index layer 4 may be directly deposited on the low refractive index layer 3 or may be laminated by bonding a plate-like member formed of the above-mentioned material to a part obtained by laminating the low refractive index layer 3 on the substrate 2.

As shown in FIG. 2, the surface of the high refractive index layer 4 is a surface on which the detection target objects S are held. Hereinafter, the surface is referred to as holding surface 4a. The holding surface 4a can be segmented into regions to which the detection target objects S are adsorbed. Hereinafter, the region to which the detection target object S is adsorbed is referred to as adsorption region, and the region to which the detection target object S is not adsorbed is referred to as non-adsorption region.

Figure 3:
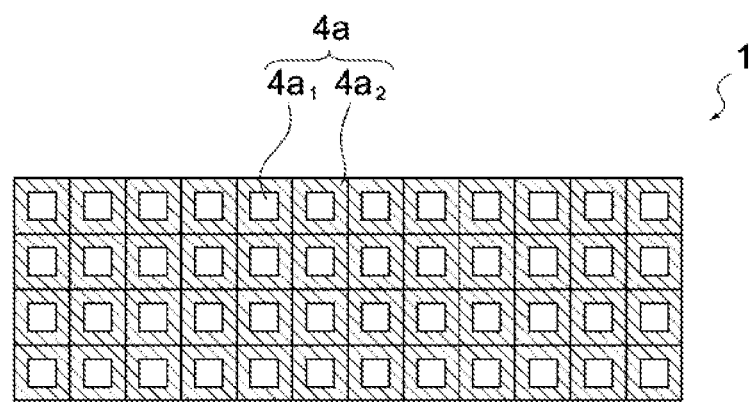
FIG. 3 A schematic diagram showing an adsorption region and non-adsorption region in the chemical sensor.

FIG. 3 is a schematic diagram showing adsorption regions $4a_1$ and non-adsorption regions $4a_2$ formed on the holding surface 4a. As shown in the figure, the adsorption regions $4a_1$ may be regions surrounded by the non-adsorption regions $4a_2$. By partitioning the holding surface 4a in this way, different types of detection target objects S can be arranged on the respective adsorption regions $4a_1$. Further, it is possible to cause the detection target objects S that cover the respective adsorption regions $4a_1$ to be opposed to the respective light detection units 21 in the one-to-one relationship.

It should be noted that the adsorption region $4a_1$ is not limited to the case where it is formed with respect to the light detection unit 21 with the one-to-one relationship, and the plurality of adsorption regions $4a_1$ may be formed to be opposed to one light detection unit 21. However, with the one-to-one relationship, it is possible to improve the detection accuracy.

It is assumed that the chemical sensor 1 in the state where surface processing is applied thereto as described above is supplied to a user, and the user use the chemical sensor 1 by covering the adsorption regions $4a_1$ with arbitrary detection target objects S, for example.

The adsorption regions $4a_1$ and the non-adsorption region $4a_2$ can be segmented by surface processing on the holding surface 4a. Specifically, in the case where the detection target objects S include a hydrophilic material, a region to which hydrophilic processing is applied can be assumed to be the adsorption region $4a_1$, and a region to which hydrophobic is applied can be assumed to be the non-adsorption region $4a_2$. In addition, in the case where the detection target objects S include a hydrophobic material, a region to which hydrophobic processing is applied can be assumed to the adsorption region $4a_1$, and a region to which hydrophilic processing is applied can be assumed to be the non-adsorption region $4a_2$.

Moreover, the adsorption regions $4a_1$ and the non-adsorption region $4a_2$ can be segmented by a coating film deposited on the holding surface 4a. Specifically, in the case where the holding surface 4a includes a material to which the detection target object S is adsorbed, by forming a coating film formed of a material to which the detection target object S is not adsorbed, a region on which the coating film is formed can be assumed to be the non-adsorption region $4a_2$ and a region on which the coating film is not formed can be assumed to be the adsorption region $4a_1$. In addition, although the details will be described later, the coating film favorably has light reflectivity, and may be an aluminum coating film, for example.

It should be noted that the entire region of the holding surface 4a can be assumed to be the adsorption region $4a_1$, and the non-adsorption region $4a_2$ may not be formed. In this case, the entire region of the holding surface 4a is covered by the detection target objects S uniformly.

[Configuration of Chemical Sensor Module]

Figure 4:
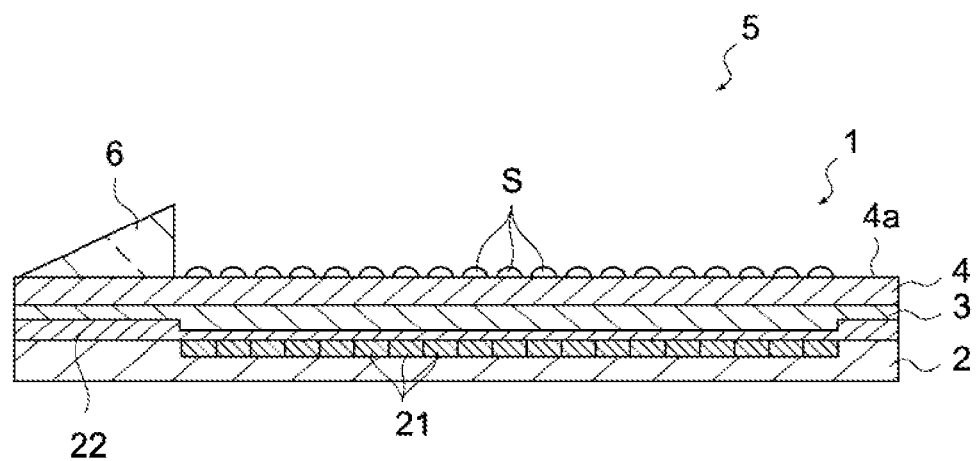
FIG. 4 A cross-sectional view showing a chemical sensor module according to the first embodiment.

The above-mentioned chemical sensor 1 can be used as a chemical sensor module. FIG. 4 is a cross-sectional view showing a chemical sensor module 5. As shown in the figure, a light introduction unit 6 is joined to the chemical sensor 1, thereby forming the chemical sensor module 5.

The light introduction unit 6 is a member that introduces light into the high refractive index layer Oat a predetermined angle. The details of the incidence angle of light will be described later. The light introduction unit 6 can be a light introduction prism joined to the high refractive index layer 4 as shown in FIG. 4, and may be another member that is capable of introducing light into the high refractive index layer 4 at a predetermined angle. The light introduction unit 6 can be joined to the high refractive index layer 4 via index matching oil or the like so that an air layer does not enter between the light introduction unit 6 and the high refractive index layer 4.

Figure 5:
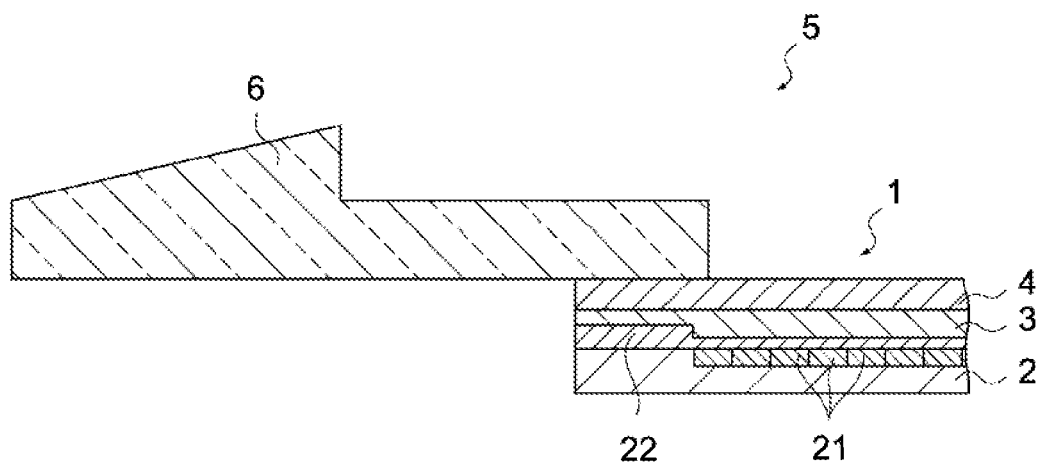
FIG. 5 A schematic diagram showing arrangement of a light introduction unit of the chemical sensor module.
Figure 6:
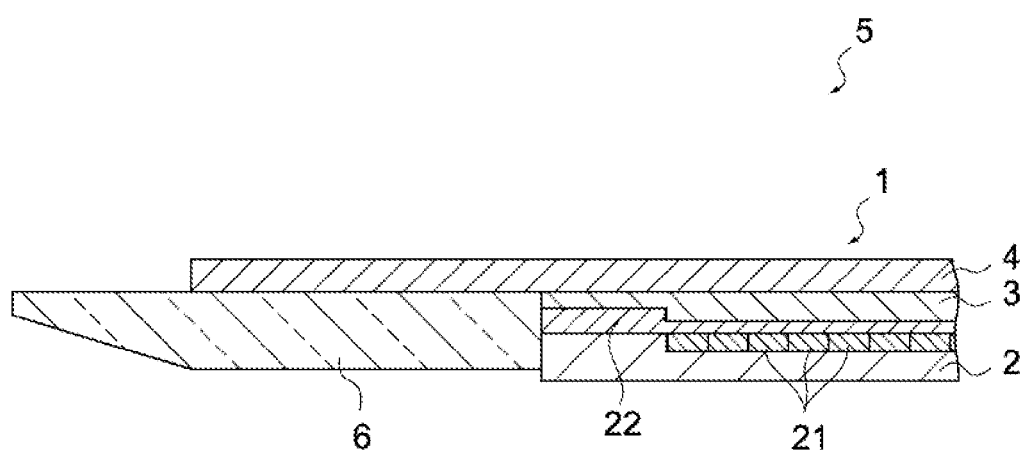
FIG. 6 A schematic diagram showing arrangement of the light introduction unit of the chemical sensor module.

The light introduction unit 6 is not necessarily arranged on the high refractive index layer 4. FIG. 5 and FIG. 6 are schematic diagrams showing different examples of arrangement of the light introduction unit 6. The light introduction unit 6 may be on the upper layer side of the high refractive index layer 4 as shown in FIG. 5, and may be on the lower layer side of the high refractive index layer 4 as shown in FIG. 6. In addition, a plurality of light introduction units 6 may be provided so that illumination light (to be described later) can be introduced into the high refractive index layer 4 from a plurality of directions.

[Configuration of Chemical Detection Apparatus]

Figure 22:
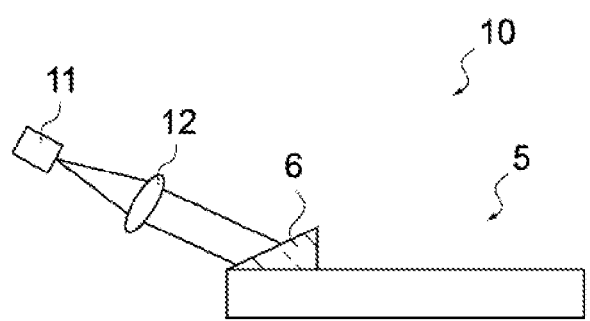
FIG. 22 A schematic diagram showing a configuration of a chemical detection apparatus according to the first embodiment.

The chemical sensor module 5 can be used as the chemical detection apparatus together with a light source. FIG. 22 is a schematic diagram showing the configuration of the chemical detection apparatus. As shown in the figure, a chemical detection apparatus 10 includes the chemical sensor module 5 and a light source 11. In addition, a lens 12 is provided between the chemical sensor module 5 and the light source 11.

The illumination light emitted from the light source 11 can be made to be parallel light by the lens 12, and can enter the high refractive index layer 4 via the light introduction unit 6. It is favorable that the incidence angle of the illumination light on the high refractive index layer 4 can be changed depending on the position or angle of the light source 11 and the lens 12.

[Detection of Target Material Using Chemical Sensor]

A method of detecting a target material using the chemical sensor 1 (and the chemical sensor module 5) will be described.

If various kinds of probe materials are adsorbed to the adsorption regions $4a_1$ and a sample including a target material is supplied to the chemical sensor 1, the target material in the sample specifically bonds to a predetermined probe material. A fluorescent label material that is capable of performing fluorescent labeling of a composite material of a target material and a probe material is supplied to the chemical sensor 1, only the detection target object S including the composite material of a target material and a probe material is fluorescent-labeled. By detecting the fluorescent light, it is possible to specify the target material included in the sample.

In addition, the target material may be subjected to fluorescent labeling in advance. In this case, because the target material that is not bonded to the probe material adsorbed to the adsorption regions $4a_1$ is removed from the chemical sensor 1, it is possible to use the fluorescent light to specify the target material, similarly to the above. In addition, the target material may be specified by applying fluorescent labeling to the probe material in advance and detecting the wavelength and change in luminance of the fluorescent light generated due to the bonding of the probe material and the target material.

As described above, the chemical sensor 1 can specify the target material by detecting fluorescent light generated from the detection target object S, it is important to measure the fluorescent light accurately. If the light detection unit 21 detects excitation light for generating fluorescent light, a value of the intensity of fluorescent light different from that of normal fluorescent light is output from the light detection unit 21. However, in the chemical sensor 1 according to the present technology, the excitation light is prevented from reaching the light detection unit 21 by a mechanism to be described later, i.e., the fluorescent light can be measured accurately.

It should be noted that here, although the description has been made that fluorescent light generated from the detection target object S by the irradiation of excitation light is detected by the light detection unit 21, but it is not limited thereto. It is only necessary that if some kind of light is applied to the detection target object S, some kind of light is generated from the detection target object S. For example, the case where scattered light is generated from the detection target object S only in the case where the detection target object S includes a specific material is conceivable.

In the following description, light applied to the detection target object S as in the above-mentioned excitation light is referred to as "illumination light", and light generated from the detection target object S by the irradiation of light as in the fluorescent light is referred to as "detection target light."

The chemical sensor 1 can be used in the following fields. The fields include chemical or biochemical analysis including analysis of biological fluid such as yolk, blood, serum and plasma, environmental analysis including analysis of water, dissolved soil extract, and dissolved plant extract, chemical production, particularly analysis in a dye solution or a reaction solution, dispersion or formulation analysis, quality protection analysis, and gene analysis.

[Operation of Chemical Sensor]

Figure 7:
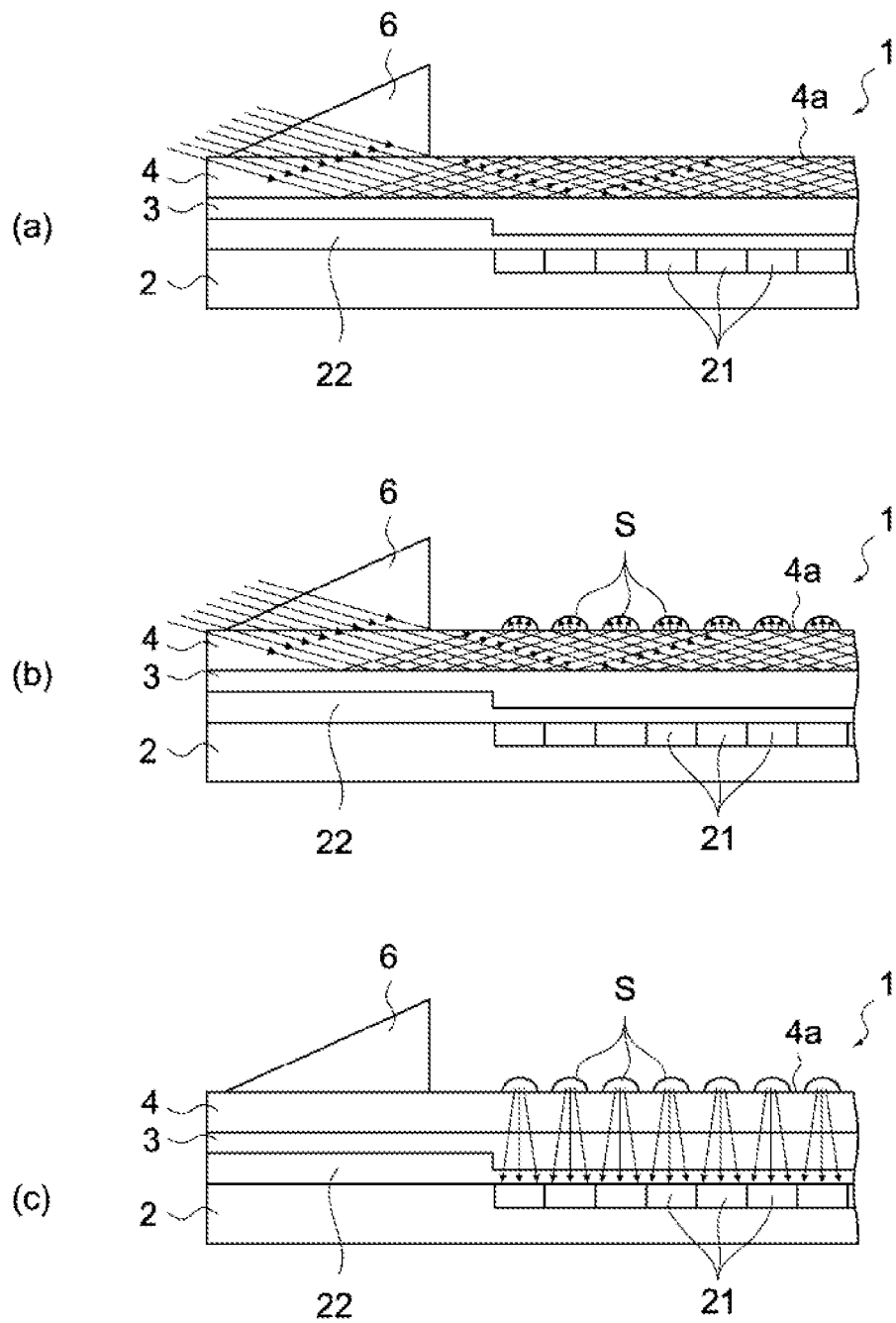
FIG. 7 A schematic diagram showing an operation of the chemical sensor according to the first embodiment.

The operation of the chemical sensor 1 (and the chemical sensor module 5) will be described. FIG. 7 is a schematic diagram showing the operation of the chemical sensor 1.

First, the case where the detection target objects S do not cover the holding surface 4a of the high refractive index layer 4 will be described. As shown in FIG. 7(a), illumination light is introduced into the high refractive index layer 4 via the light introduction unit 6. The illumination light enters the holding surface 4a of the high refractive index layer 4 within a predetermined angle range, but the angle range will be described later.

Here, because the refractive index of the high refractive index layer 4 (third refractive index n3) is larger than air (refractive index n=1) and the refractive index of the low refractive index layer 3 (the second refractive index n2) as described above, total reflection of the illumination light that has entered within the appropriate angle range is repeated on the interface of the high refractive index layer 4 and air and the interface of the high refractive index layer 4 and the low refractive index layer 3, and the illumination light propagates in the high refractive index layer 4 as shown in FIG. 7(a). That is, in this state, the illumination light propagates in the high refractive index layer 4 without leaking to the outside.

Next, the case where the detection target objects S cover the holding surface 4a will be described. As shown in FIG.

7(*b*), by causing the illumination light to enter the high refractive index layer 4 at an appropriate incident angle, the illumination light that has reached the adsorption regions 4a₁ on which the detection target object S is provided is refracted and transmitted thereto without being totally reflected thereon, and then enters the detection target object S. This is because the refractive index of the detection target object S (first refractive index n1) is larger than the refractive index of air.

On the other hand, light that has reached the non-adsorption region 4a₂ on which the detection target object S is not provided is totally reflected thereon similarly to the above, and propagates in the high refractive index layer 4 again.

That is, it is possible to cause the illumination light to enter the detection target object S in a region (the adsorption regions 4a₁) on which the detection target object S exists, and cause the illumination light to be totally reflected on a region (the non-adsorption region 4a₂) on which the detection target object S does not exist. In addition, also in this case, because the refractive index of the low refractive index layer 3 (the second refractive index n2) is smaller than the refractive index of the detection target object S (the first refractive index n1), the illumination light is totally reflected on the interface of the high refractive index layer 4 and the low refractive index layer 3.

Therefore, in this state, the illumination light enters only the detection target object S while propagating in the high refractive index layer 4. Because the illumination light does not leak from the non-adsorption region 4a₂ on which the detection target object S does not exist, optical energy is not lost. Because the illumination light does not reach the light detection unit 21, the illumination light is not detected by the light detection unit 21.

Moreover, also in the case where the non-adsorption region 4a₂ is formed of a coating film including a material to which the detection target object S is not adsorbed, by using the coating film having light reflectivity, it is possible to prevent the illumination light from leaking from the non-adsorption region 4a₂. Also in this case, it is possible to prevent optical energy to be lost or the illumination light to be detected by the light detection unit 21.

As shown in FIG. 7(*c*), the illumination light that has entered the detection target object S generates the detection target light (fluorescent light or the like) from the detection target object S, and the detection target light is detected by the light detection unit 21. Although the detection target light is emitted from the detection target object S in all directions, a part thereof is transmitted through the high refractive index layer 4 and the low refractive index layer 3 and is detected by the light detection unit 21. It should be noted that because the detection target light enters the high refractive index layer 4 at a steep incidence angle, it reaches the light detection unit 21 without being totally reflected on the interface of the high refractive index layer 4 or the like.

As described above, according to the configuration of the chemical sensor 1 of this embodiment, the illumination light that has entered the high refractive index layer 4 does not reach the light detection unit 21 and it is possible to prevent the illumination light from being detected by the light detection unit 21. Furthermore, the illumination light that has entered the high refractive index layer 4 does not attenuate except when it enters the detection target object S. That is, it is possible to use the optical energy effectively.

[Regarding Incidence Angle of Illumination Light]

Although the case where the illumination light enters the high refractive index layer 4 at an appropriate incidence angle in the operation of the chemical sensor 1 described above has been described, the incidence angle will be described in detail.

Figure 8:
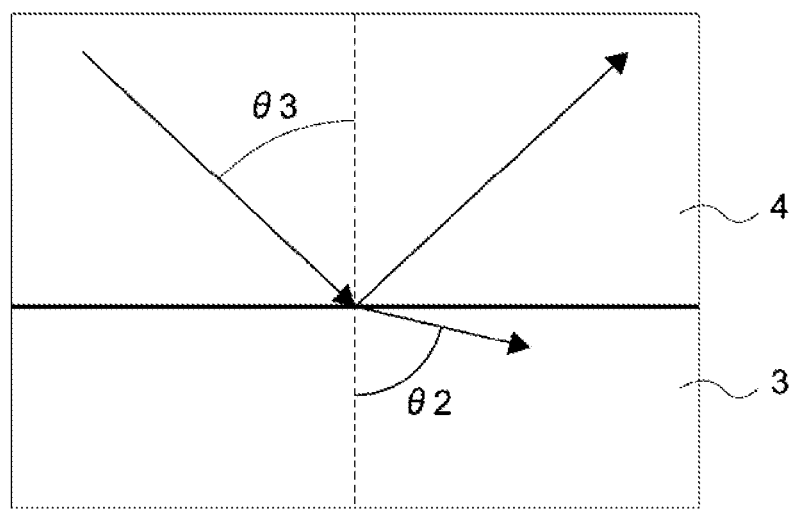
FIG. 8 A schematic diagram showing an interface of a high refractive index layer and a low refractive index layer of the chemical sensor.

FIG. 8 is a schematic diagram showing the interface of the high refractive index layer 4 and the low refractive index layer 3. Assuming that the incidence angle of the illumination light (shown by arrows in the figure) on the interface is an angle θ3 and an output angle of the illumination light from the interface is an angle θ2, the relationship of the following equation (1) is established according to the Snell's law.

$$n3 \times \sin \theta 3 = n2 \times \sin \theta 2 \quad (1)$$

As described above, because the third refractive index n3 is larger than the second refractive index n2, the angle θ3 exists such that the angle θ2 is not less than 90°. In this state, the illumination light cannot be refracted and transmitted from the high refractive index layer 4 to the low refractive index layer 3, is totally reflected, and returns to the high refractive index layer 4.

Figure 9:
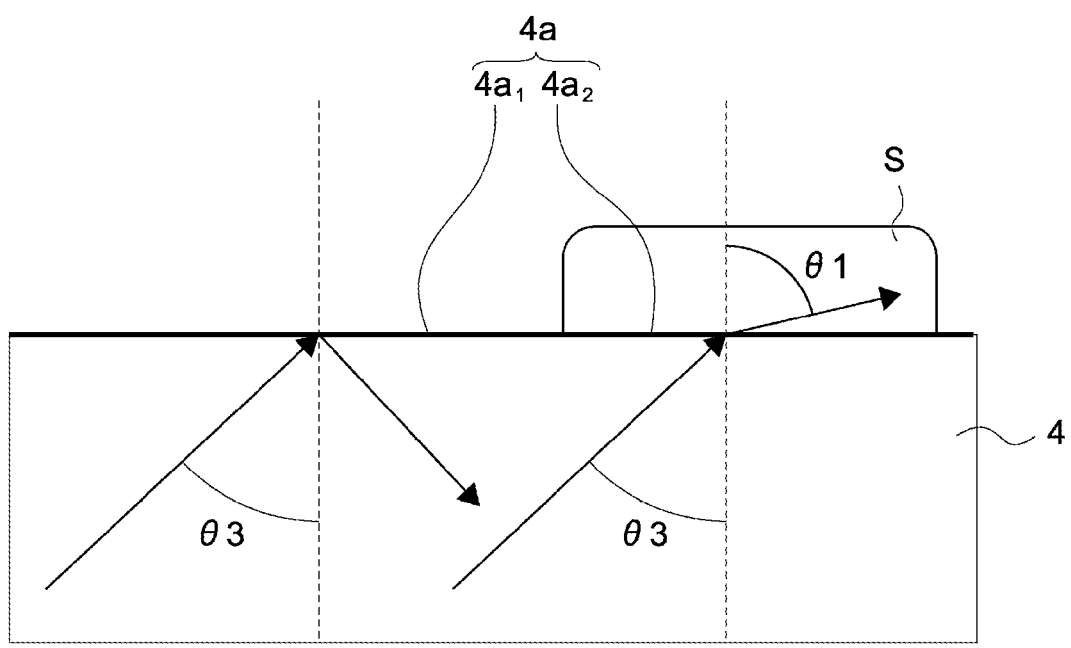
FIG. 9 A schematic diagram showing an interface of the high refractive index layer and a detection target object of the chemical sensor.

FIG. 9 is a schematic diagram showing the interface of the high refractive index layer 4 and the detection target object S. In the non-adsorption region 4a₂ that is not covered by the detection target object S, because the refractive index of air n=1, and is smaller than the third refractive index n3, the illumination light is totally reflected at the angle θ3 such that the angle θ2 is not less than 90°.

Moreover, the illumination light is refracted and transmitted from the interface to the detection target object S in the adsorption regions 4a₁, as described above. Assuming that an output angle of the illumination light from the interface is an angle θ1, the following equation (2) is satisfied similarly to the equation (1).

$$n3 \times \sin \theta 3 = n2 \times \sin \theta 2 = n1 \times \sin \theta 1 \quad (2)$$

Because the first refractive index n1 is larger than the second refractive index n2, θ1<90° from the equation (2) even in the case where the angle θ2 is 90°. That is, the illumination light is refracted and transmitted to the detection target object S.

As described above, the incidence angle of the illumination light on the high refractive index layer 4 can be selected depending on the respective values of the first refractive index n1, the second refractive index n2, and the third refractive index n3. Accordingly, it is possible to cause the illumination light to be totally reflected on the interface of the low refractive index layer 3 and the non-adsorption region 4a₂ and to cause the illumination light to be refracted and transmitted on the interface with the adsorption regions 4a₁ (detection target object S).

FIG. 10 is a table showing incidence angles at which total reflection of the illumination light occurs with respect to the values of the first refractive index n1 (detection target object S), the second refractive index n2 (low refractive index layer 3), and the refractive index 3 (high refractive index layer 4). For example, in the case where the third refractive index n3 is 1.9, the second refractive index n2 is 1.3, and the first refractive index n1 is 1.4, from the table, total reflection occurs if the incidence angle is not less than 43.2°. In addition, if the incidence angle is less than 47.5°, refraction and transmission to the detection target object S occurs. That is, if the incidence angle is not less than 43.2° and less than 47.5°, it is possible to cause the illumination light to be refracted and transmitted to only the detection target object S, and to be totally reflected on another interface.

[Method of Manufacturing Chemical Sensor]

Figure 11:
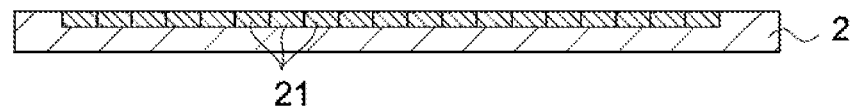
FIG. 11 A schematic diagram showing a method of manufacturing the chemical sensor.
Figure 11:
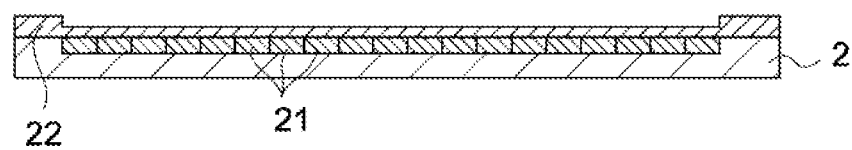
Figure 11:
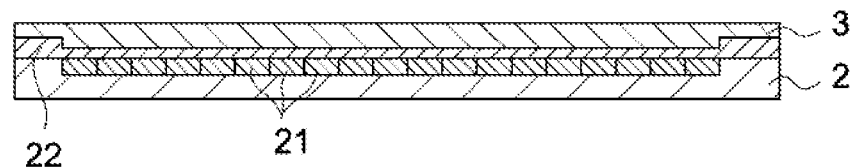
Figure 11:
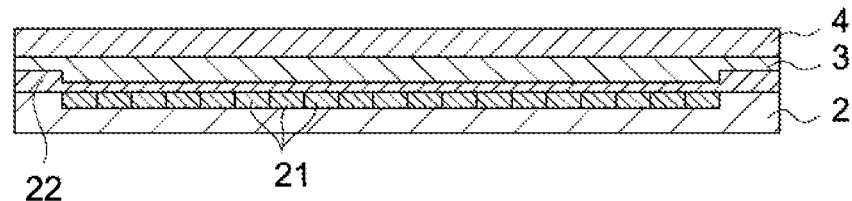

A method of manufacturing the chemical sensor 1 (and the chemical sensor module 5) will be described. FIG. 11 is a schematic diagram showing a method of manufacturing the chemical sensor 1.

As shown in FIG. 11(a), the light detection unit 21 including an impurity region is formed on a surface of the substrate 2 formed of, for example, single crystal silicon by ion-implantation from a mask and the subsequent heat treatment, and the like. Next, as shown in FIG. 11(b), the protective insulating film 22 is formed on the substrate 2 on which the light detection unit 21 is formed.

Next, as shown in FIG. 11(c), the low refractive index layer 3 is laminated on the protective insulating film 22. The low refractive index layer 3 can be formed by, for example, applying raw material resin by a method such as spin coating and drying it.

Furthermore, as shown in FIG. 11(d), the high refractive index layer 4 is laminated on the low refractive index layer 3. The low refractive index layer 3 can be formed by, for example, applying raw material resin by a method such as spin coating and drying it. It should be noted that the high refractive index layer 4 can be formed by printing or applying a resin sheet.

Figure 12:
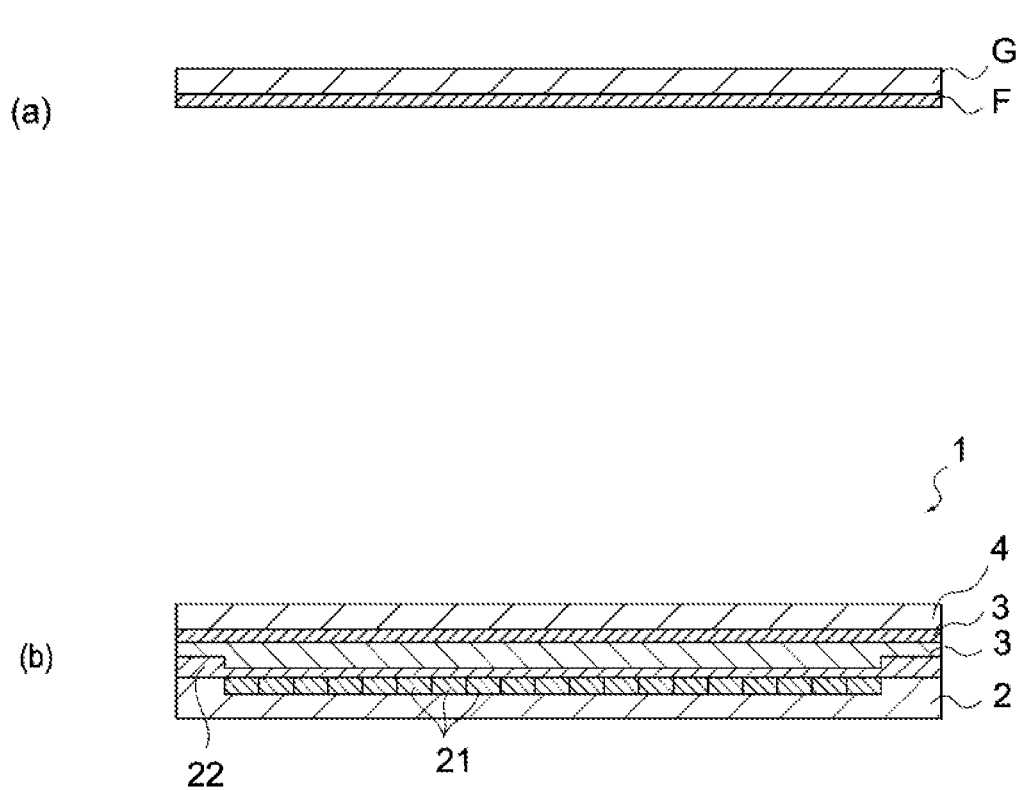
FIG. 12 A schematic diagram showing another method of manufacturing the chemical sensor.

Moreover, the high refractive index layer 4 can be formed by applying a plate-like member on the low refractive index layer 3. FIG. 12 is a schematic diagram showing a method of manufacturing the chemical sensor 1 in accordance with this method. Specifically, thin plate glasses such as L-LAH84 (n=1.80), L-NBH (n=1.92), S-LAH79 (n=2.0), and L-BBH1 (n=2.10), which are manufactured by OHARA INC. and have high refractive index, are prepared.

As shown in FIG. 12(a), to a thin plate glass G, a resin sheet F having a low (n=about 1.4) refractive index is applied by vacuum lamination. Next, as shown in FIG. 12(b), the thin plate glass G is applied to the low refractive index layer 3 by vacuum lamination with the resin sheet F side being the low refractive index layer 3 side.

Next, the adsorption regions $4a_1$ and the non-adsorption region $4a_2$ are formed on the holding surface $4a$ of the high refractive index layer 4. In the case where a hydrophilic material is scheduled to be used as the detection target object S, a region to which hydrophilic processing is applied can be the adsorption regions $4a_1$, and a region to which hydrophobic processing is applied can be the non-adsorption region $4a_2$. In addition, in the case where a hydrophobic material is scheduled to be used as the detection target object S, a region to which hydrophobic processing is applied can be the adsorption regions $4a_1$, and a region to which hydrophilic processing is applied can be the non-adsorption region $4a_2$. Furthermore, a metal thin film is formed on the holding surface $4a$, which can be the non-adsorption region $4a_2$.

Figure 13:
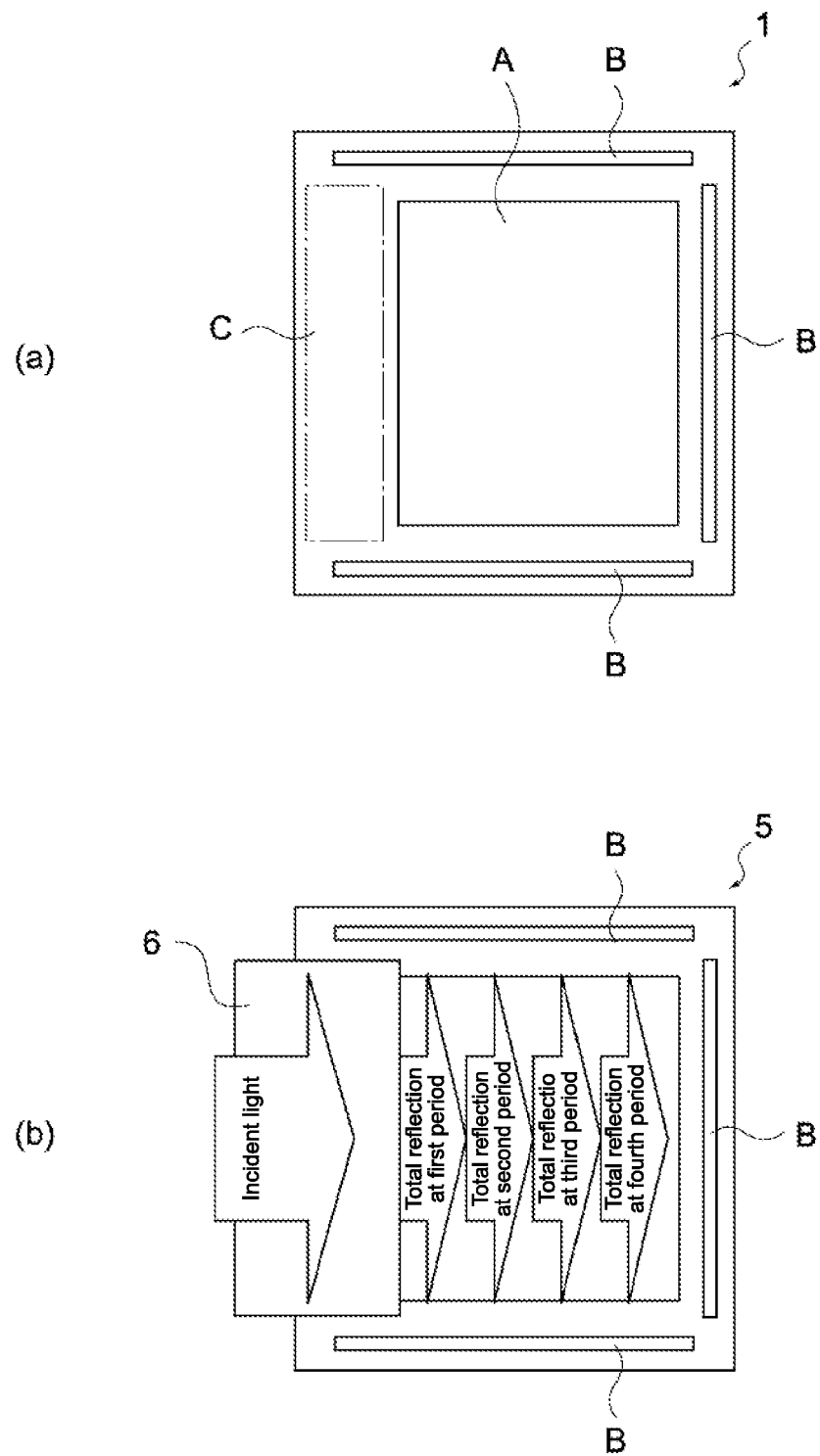
FIG. 13 A schematic diagram showing a mode in which the light introduction unit is joined to the chemical sensor.

In this way, the chemical sensor 1 can be manufactured. Furthermore, by joining the light introduction unit 6 to the chemical sensor 1, the chemical sensor module 5 can be manufactured. FIG. 13 is a schematic diagram showing a mode in which the light introduction unit 6 is joined to the chemical sensor 1. As shown in FIG. 13(a), in the chemical sensor 1, a sensor region A in which the light detection unit 21 is formed is provided, and terminals B for joining the chemical sensor 1 to another member are provided on three sides thereof.

In this case, the light introduction unit 6 is joined to a region for light introduction unit C on which the terminal B is not provided, via index matching oil, for example.

Accordingly, as shown in FIG. 13(b), the light that has entered the light introduction unit 6 propagates in the high refractive index layer 4 periodically. In this way, the chemical sensor module 5 can be manufactured.

Second Embodiment

A chemical sensor according a second embodiment of the present technology will be described. It should be noted that in this embodiment, the same configurations as those of the chemical sensor according to the first embodiment will be denoted by the same reference symbols and a description thereof will be omitted. The chemical sensor according to this embodiment has the same layered structure as the chemicals sensor according to the first embodiment, but has an adsorption region that is covered by a detection target object, which is different from that of the first embodiment.

Figure 14:
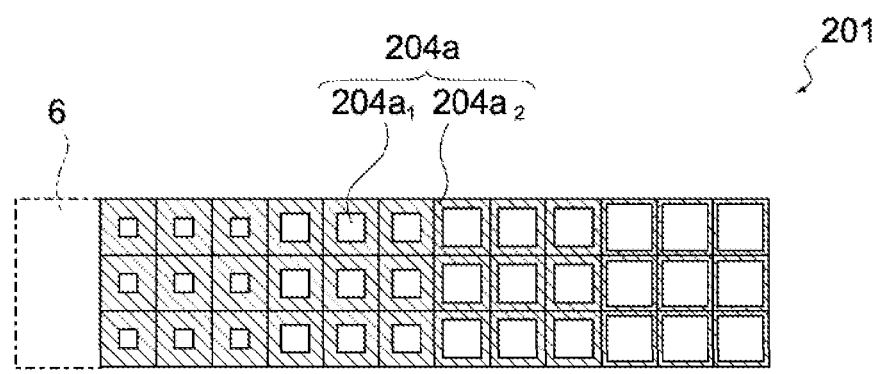
FIG. 14 A schematic diagram showing a configuration of a chemical sensor according to a second embodiment.

FIG. 14 is a schematic diagram showing a chemical sensor 201 according to this embodiment. As shown in the figure, adsorption regions $204a_1$ of the chemical sensor 201 are formed such that the area thereof increases for every three columns from the side of the light introduction unit 6. In other words, non-adsorption regions $204a_2$ that separate the adsorption regions $204a_1$ are formed such that they get thin for every three columns. It should be noted that the area of the adsorption regions $204a_1$ is not limited to the case of increasing for every three columns, and can increase for every columns, ever two columns, or every multiple columns.

By making the adsorption region $204a_1$ to have such a configuration, it is possible to cause uniform amounts of illumination light to enter the detection target objects S. As described in the first embodiment, by entering the detection target object S, the illumination light that propagates in the high refractive index layer 4 attenuates as it moves away from the light introduction unit 6. Therefore, the intensity of the illumination light per unit area decreases in the adsorption region $204a_1$ that is distant from the light introduction unit 6 as compared with the adsorption region $204a_1$ that is close to the light introduction unit 6.

Accordingly, by increasing the area of the adsorption region $204a_1$ opposed to the light detection unit 21 such that the area increases with the increasing distance from the light introduction unit 6, it is possible to cause uniform amounts of illumination light to enter the adsorption regions $204a_1$.

Hereinafter, the area ratio (opening ratio) of the adsorption region $204a_1$ and the non-adsorption region $204a_2$ will be described in detail. As described above, the illumination light introduced into the high refractive index layer 4 propagates in the high refractive index layer 4 while being totally reflected on the interface. The illumination light is emitted from the adsorption region $204a_1$ (hereinafter, opening) for every total reflection. Therefore, assuming that the number of times of total reflection is n, the proportion of the size of a side of the adsorption region $204a_1$ (hereinafter, opening size) is Xn, and the amount of emitted illumination light from the opening at the n-th total reflection is In, the following equation (3) is satisfied.

$$I1 = X1^2$$
$$I2 = (1 - I1)X2^2$$
$$I3 = (1 - I2)X3^2$$
$$In = (1 - I(n-1))Xn^2$$
$$\vdots$$
(3)

Moreover, if all illumination light is considered to be emitted at the time of the propagation of the illumination up to the n-th total reflection, assuming that the total amount of illumination light is 1 and the amount of illumination light emitted from the opening of each place is obtained by dividing the total amount illumination light by the number of times of total reflection, i.e., equal, the following formula (4) is satisfied.

$$1 = I1/n + I2/n + I3/n + \ldots + In/n \quad (4)$$

Here, the following equation (5) is satisfied.

$$I1/n = I2/n = I3/n = \ldots = In/n \quad (5)$$

FIG. 15 is a table showing the amount of illumination light in the case where the number of times of total reflection is 4 and the illumination light is applied to the entire surface of the holding surface 4a. As shown in the figure, by setting the ratio of the opening size to 50% in the case of openings within the range of the 1st total reflection, to 57.7% in the case of openings within the range of the 2nd total reflection, to 70.7% in the case of openings within the range of the 3rd total reflection, and to 100% in the case of openings within the range of the 4th total reflection, it is possible to equally illuminate the entire surface.

It should be noted that because the opening is connected to an adjacent opening in the case where the opening size is 100%, there is a need to set an upper limit of the opening size actually. Therefore, the case where the maximum opening size is set to about 90% is conceivable. FIG. 16 is a table showing the amount of illumination light in the case where the number of times of total reflection is 4, the illumination light is applied to the entire surface of the holding surface 4a, and the opening size is about 90%.

Moreover, the case where the number of times of total reflection is 8 and the illumination light is applied to the entire surface of the holding surface 4a is as follows. FIG. 17 is a table showing the amount of illumination light in the case where the number of times of total reflection is 8 and the illumination light is applied to the entire surface of the holding surface 4a.

As described above, by increasing the area of the adsorption region $204a_1$ with the increasing distance from the light introduction unit 6, it is possible to cause uniform amounts of illumination light to enter the detection target objects S.

Third Embodiment

A chemical sensor according to a third embodiment of the present technology will be described. It should be noted that in this embodiment, the same configurations as those of the chemical sensor according to the first embodiment will be denoted by the same reference symbols and a description thereof will be omitted. The chemical sensor according to this embodiment is obtained by adding on-chip lenses and color filters to the layered structure of the chemical sensor according to the first embodiment.

Figure 18:
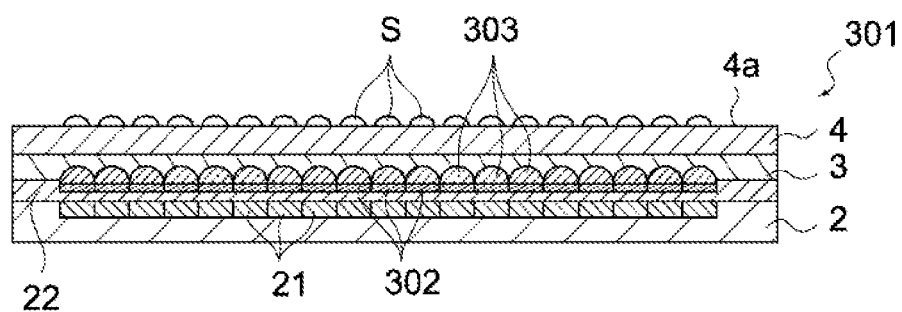
FIG. 18 A schematic diagram showing a configuration of a chemical sensor according to a third embodiment.

FIG. 18 is a cross-sectional view showing the configuration of a chemical sensor 301 according to this embodiment. As shown in the figure, the chemical sensor 301 includes color filters 302 and on-chip lenses 303 in addition to the substrate 2, the low refractive index layer 3, and the high refractive index layer 4. The color filters 302 and the on-chip lenses 303 are formed on the substrate 2 in the stated order.

The color filters 302 can be one that has optical properties in which the detection target light is transmitted and the illumination light is blocked. As described above, the illumination light does not leak from the high refractive index layer 4 to the side of the light detection unit 21 in principle. However, the case where the illumination light that has entered the detection target object S is reflected or scattered in the detection target object S and travels to the side of the detection target object S is also conceivable. Even in such a case, because the illumination light can be blocked by the color filters 302, it is possible to prevent the illumination light from being detected by the light detection unit 21.

Moreover, the color filters 302 may have different transmission wavelengths for the regions opposed to the detection target objects S. Accordingly, in the case where the detection target light generated from the adjacent detection target objects S has different wavelengths, it is possible to block the detection target light from the adjacent detection target objects S and to prevent cross talk from occurring.

Figure 23:
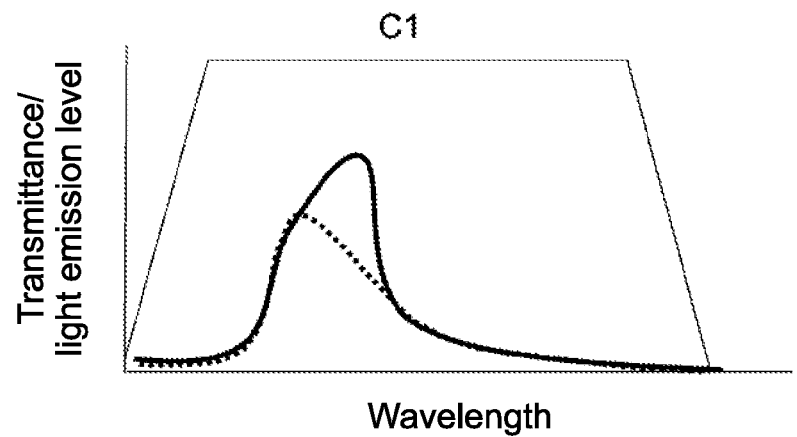
FIG. 23 A graph showing an example of light emission spectrum of detection target light and light transmittance of a color filter.
Figure 23:
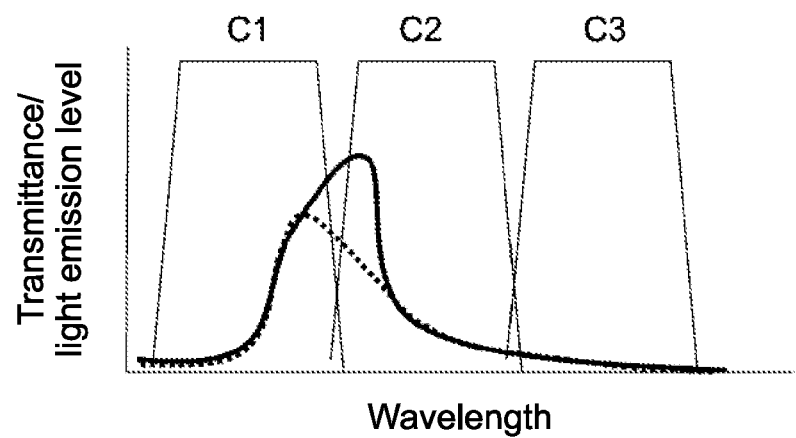
Figure 24:
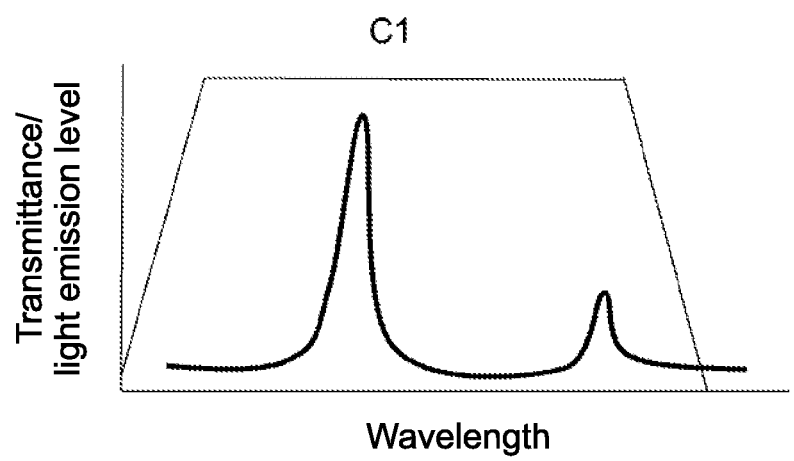
FIG. 24 A graph showing an example of light emission spectrum of detection target light and light transmittance of a color filter.
Figure 24:
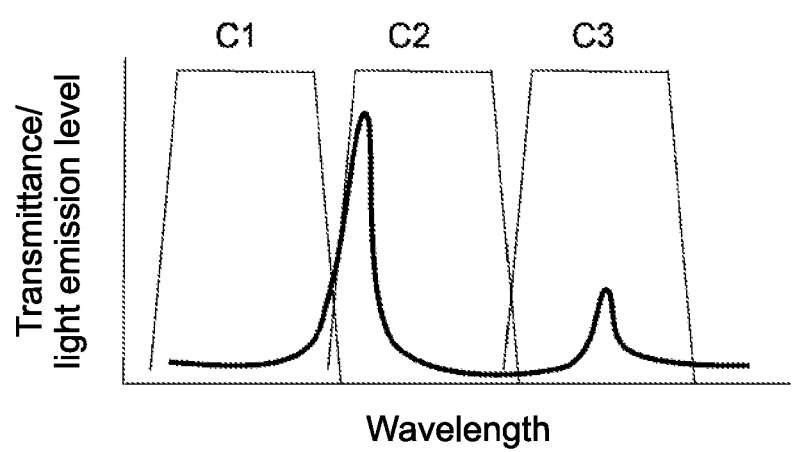

Furthermore, by forming one adsorption region $4a_1$ so as to be opposed to a plurality of light detection units 21 and providing the color filters 302 having different colors to the light detection units 21, it is possible to confirm the properties of light emission spectrum of the detection target light in the detection target object S in one adsorption region $4a_1$. FIG. 23 and FIG. 24 are each a graph showing an example of the light emission spectrum of the detection target light and light transmittance of the color filter 302.

FIG. 23(a) and FIG. 24(a) each show a transmission wavelength (C1) in the case where the color filters 302 have one color, and FIGS. 23(b) and FIG. 24(b) each show transmission wavelengths (C1, C2, and C3) in the case where the color filters 302 have 3 colors. As shown in FIG. 23(b) and FIG. 24(b), in the case where the detection target light includes a plurality of wavelength components, the difference can be discriminated.

The on-chip lenses 303 collects the incident detection target light on the light detection unit 21. The on-chip lenses 303 may have a hemispherical shape in which the side of the detection target object S is spherical, and may have a lens shape different from this. Moreover, the respective on-chip lenses 303 may be provided to be opposed to the light detection unit 21. With the on-chip lenses 303, it is possible to collect the detection target light isotropically emitted from the detection target object S on the light detection unit 21 and to improve the detection accuracy of the detection target light.

The chemical sensor 301 is configured as described above. It should be noted that either one of the color filters 302 and the on-chip lenses 303 may be provided.

Figure 19:
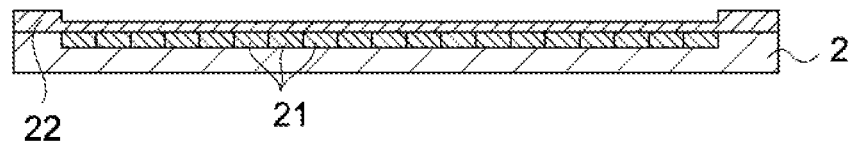
FIG. 19 A schematic diagram showing a method of manufacturing the chemical sensor.
Figure 19:
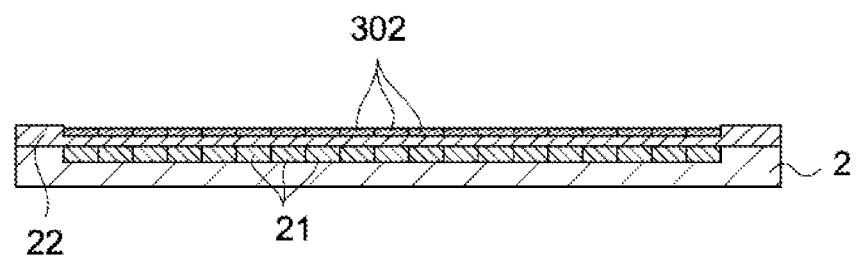
Figure 19:
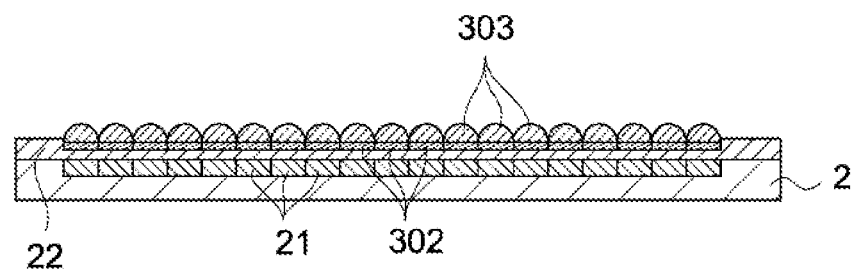
Figure 20:
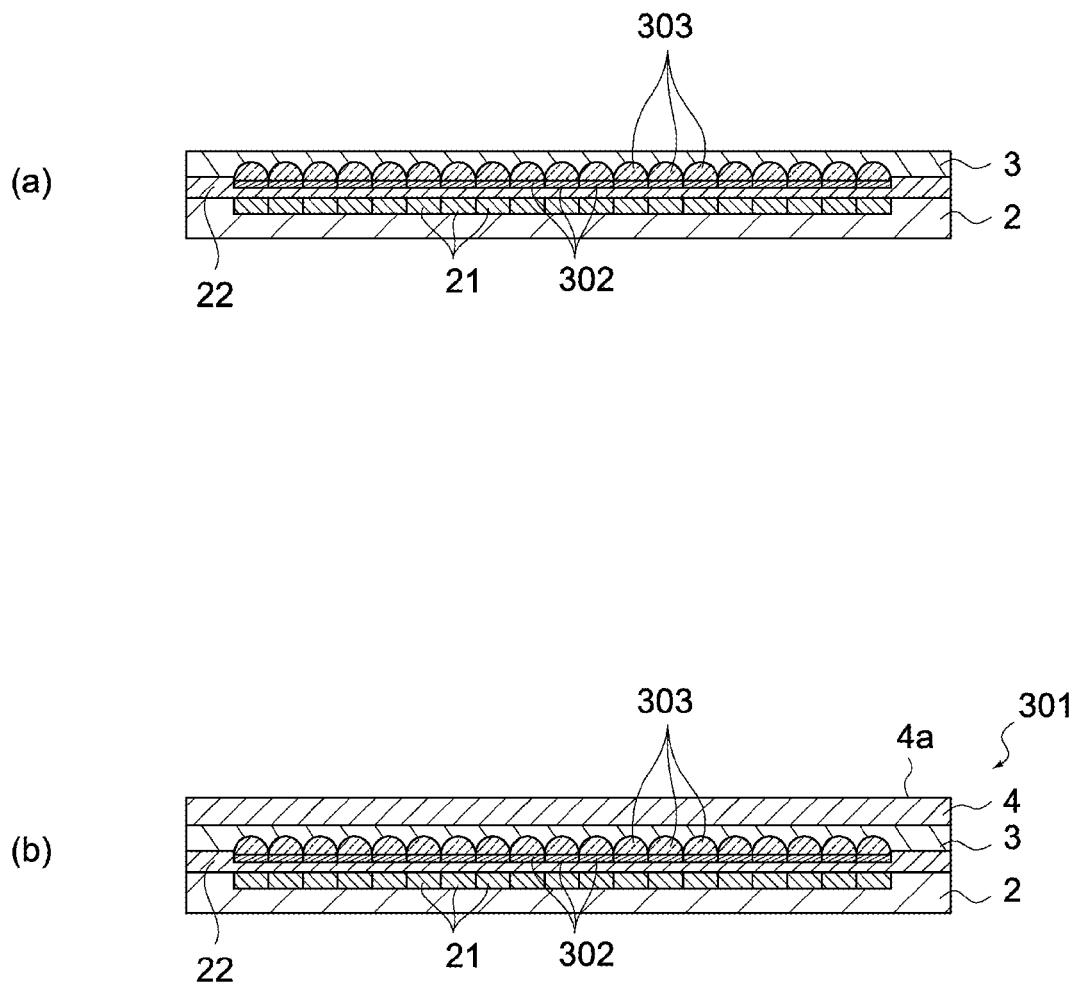
FIG. 20 A schematic diagram showing a method of manufacturing the chemical sensor.

A method of manufacturing the chemical sensor 301 will be described. FIG. 19 and FIG. 20 are each a schematic diagram showing a method of manufacturing the chemical sensor 301.

As shown in FIG. 19(a), the light detection unit 21 is formed on the substrate 2 and the protective insulating film 22 is formed thereon, in the same way as that in the first embodiment. The protective insulating film 22 is formed to have a film thickness adjusted so that the on-chip lens 303 is focused on the light detection unit 21, taking into account of the focal length of the on-chip lens 303.

Next, as shown in FIG. 19(b), the color filters 302 are formed on the protective insulating film 22. The color filters 302 are formed by spin coating, for example. Furthermore, as shown in FIG. 19(c), the on-chip lenses 303 are formed on the color filters 302. The on-chip lenses 303 can be formed by a melt flow method.

Specifically, a lens material, e.g., silicon nitride, is deposited on the color filters 302, and a resist pattern having an island shape is formed thereon. Next, the resist pattern is fluidized by heat treatment, and the resist pattern is molded into a convex lens shape using surface tension. By etching the resist pattern and the lens material from its upside, the lens shape of the resist pattern is transferred to the lens material and the lens material can be processed into a lens shape.

Next, as shown in FIG. 20(a), the low refractive index layer 3 is laminated so that the on-chip lenses 303 are embedded. The low refractive index layer 3 can be formed by a spin coating method. For example, in the case where fluorine-containing polysiloxane resin (refractive index n1=1.42) is used as the material of the low refractive index layer 3, this resin is dissolved in propylen glycol monomethyl ether acetate (PEGMEA) being a solvent. The saturated solubility of fluorine-containing polysiloxane resin in PEGMEA is small, and the solution has extremely low viscosity. However, here, it is only necessary that the on-chip lenses 303 having a lens shape are embedded and the surface is flat. For example, the solution is applied such that the film thickness is about 1 μm from the top of the on-chip lens 303. By using the solution having low viscosity as described above, it is possible to improve the embeddability of the on-chip lenses 303 and to prevent a void (cavity) from being formed.

After that, a solvent in the solution is dried and removed by heat treatment at 120° C. for 1 minute, and the fluorine-containing polysiloxane resin is sufficiently cured by heat treatment at 230° C. for 5 minutes. In this way, the on-chip lenses 303 having a lens shape are embedded, and the low refractive index layer 3 whose surface is molded into flat can be formed.

Next, as shown in FIG. 20(b), the high refractive index layer 4 is laminated on the low refractive index layer 3. The high refractive index layer 4 can be laminated by a spin coating method, for example. It should be noted that the high refractive index layer 4 can be formed also by printing, applying a resin sheet, or applying a plate-like member.

In this way, the chemical sensor 301 can be manufactured. By joining the light introduction unit 6 to the chemical sensor 301 in the same way as that in the first embodiment, the chemical sensor module can be obtained.

Fourth Embodiment

A chemical sensor according to a fourth embodiment of the present technology will be described. It should be noted that in this embodiment, the same configurations as those of the chemical sensor according to the first embodiment will be denoted by the same reference symbols and a description thereof will be omitted. The chemical sensor according to this embodiment is obtained by adding light blocking walls to the layered structure of the chemical sensor according to the first embodiment.

Figure 21:
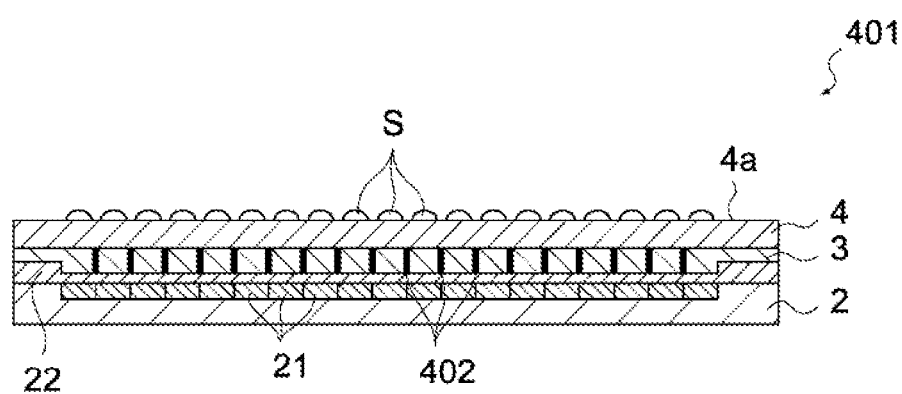
FIG. 21 A cross-sectional view showing a configuration of a chemical sensor according to a fourth embodiment.

FIG. 21 is a cross-sectional view showing the configuration of a chemical sensor 401 according to this embodiment. As shown in the figure, the chemical sensor 401 includes light blocking walls 402 in addition to the substrate 2, the low refractive index layer 3, and the high refractive index layer 4. The light blocking walls 402 are formed in the low refractive index layer 3 in a direction perpendicular to the layer.

The light blocking walls 402 block the detection target light from the adjacent detection target objects S. The light blocking walls 402 are formed of a material that is capable of blocking at least the wavelength of the detection target light, and can be arranged such that the low refractive index layer 3 is partitioned into areas opposed to the light detection units 21. In addition, the light blocking walls 402 can be provided for every a plurality of light detection units 21.

The light blocking walls 402 can be formed by laminating the low refractive index layer 3 before patterning the low refractive index layer 3, and filling a material. In addition, other than that, the low refractive index layer 3 can be formed by forming the light blocking walls 402 on the substrate 2 in advance and filling a material therein.

With the light blocking walls 402, the detection target light that has entered from the adjacent detection target object S is blocked, i.e., it is possible to prevent the cross talk of the light detection unit 21 from occurring. In the case where the light blocking walls 402 are formed in the high refractive index layer 4, the illumination light that propagates in the high refractive index layer 4 is blocked. However, by forming the light blocking walls 402 in the low refractive index layer 3, it is possible to introduce the illumination light without hindering the propagation of the illumination light.

It should be noted that the light blocking walls 402 may be added to the chemical sensor described in the third embodiment. In this case, the light blocking walls 402 can be arranged such that the on-chip lenses 303 are partitioned. In addition to the light collection with the on-chip lenses 303, it is possible to further prevent cross talk from occurring.

The present technology is not limited to the above-mentioned embodiments and various modifications can be made without departing from the gist of the present technology.

It should be noted that the present technology may also take the following configurations.

(1) A chemical sensor, including:
  a substrate;
  a low refractive index layer that is laminated on the substrate and has a second refractive index smaller than a first refractive index that is a refractive index of a detection target object;
  a high refractive index layer in which illumination light propagates, which is laminated on the low refractive index layer, has a third refractive index larger than the first refractive index, and includes a holding surface on which the detection target object is held; and
  a light detection unit that is provided on the substrate and detects detection target light generated from the detection target object by the illumination light.

(2) The chemical sensor according to (1) above, in which
  the holding surface has adsorption regions to which the detection target object is adsorbed and non-adsorption regions to which the detection target object is not adsorbed.

(3) The chemical sensor according to (1) or (2) above, in which
  the adsorption regions are separated by the non-adsorption regions.

(4) The chemical sensor according to any one of (1) to (3) above, in which
  the light detection unit includes a plurality of light detection units, and the adsorption regions are opposed to the plurality of light detection units, respectively.

(5) The chemical sensor according to any one of (1) to (4) above, in which
  the light detection unit includes a plurality of light detection units, and the adsorption regions are opposed to the plurality of respective light detection units, respectively.

(6) The chemical sensor according to any one of (1) to (5) above, in which
  the adsorption regions are formed in such a way that an area thereof is increased along a direction in which the illumination light propagates.

(7) The chemical sensor according to any one of (1) to (6) above, in which
the adsorption regions are formed by hydrophilic processing applied to the holding surface, and
the non-adsorption regions are formed by hydrophobic processing applied to the holding surface.
(8) The chemical sensor according to any one of (1) to (7) above, in which
the adsorption regions are formed by hydrophobic processing applied to the holding surface, and the non-adsorption regions are formed by hydrophilic processing applied to the holding surface.
(9) The chemical sensor according to any one of (1) to (8) above, in which
the non-adsorption regions are covered by a coating film to which the detection target object is not adsorbed, and
the adsorption regions are not covered by the coating film.
(10) The chemical sensor according to any one of (1) to (9) above, in which
the coating film has light reflectivity.
(11) The chemical sensor according to any one of (1) to (10) above, further including
a color filter that is provided between the light detection unit and the low refractive index layer, and blocks wavelengths other than that of the detection target light.
(12) The chemical sensor according to any one of (1) to (11) above, further including
an on-chip lens that is provided between the light detection unit and the low refractive index layer, and collects the detection target light on the light detection units.
(13) The chemical sensor according to any one of (1) to (12) above, further including
light blocking walls that are provided on the low refractive index layer and partition the low refractive index layer into areas opposed to the respective light detection units.
(14) The chemical sensor according to any one of (1) to (13) above, in which
the illumination light is excitation light, and
the detection target light is fluorescent light.
(15) A chemical sensor module, including:
a chemical sensor including
a substrate,
a low refractive index layer that is laminated on the substrate and has a second refractive index smaller than a first refractive index that is a refractive index of a detection target object,
a high refractive index layer in which illumination light propagates, which is laminated on the low refractive index layer, has a third refractive index larger than the first refractive index, and includes a holding surface on which the detection target object is held, and
a light detection unit that is provided on the substrate and detects detection target light generated from the detection target object by the illumination light; and
a light introduction unit that is joined to the chemical sensor and introduces the illumination light into the high refractive index layer.
(16) A chemical detection apparatus, including:
a chemical sensor module including
a chemical sensor including
a substrate,
a low refractive index layer that is laminated on the substrate and has a second refractive index smaller than a first refractive index that is a refractive index of a detection target object,
a high refractive index layer in which illumination light propagates, which is laminated on the low refractive index layer, has a third refractive index larger than the first refractive index, and includes a holding surface on which the detection target object is held, and
a light detection unit that is provided on the substrate and detects detection target light generated from the detection target object by the illumination light, and
a light introduction unit that is joined to the chemical sensor and introduces the illumination light into the high refractive index layer; and
a light source that applies the illumination light to the light introduction unit.
(17) A chemical detection method, including:
preparing a chemical sensor including
a substrate,
a low refractive index layer that is laminated on the substrate and has a second refractive index smaller than a first refractive index that is a refractive index of a detection target object,
a high refractive index layer in which illumination light propagates, which is laminated on the low refractive index layer, has a third refractive index larger than the first refractive index, and includes a holding surface on which the detection target object is held, and
a light detection unit that is provided on the substrate and detects detection target light generated from the detection target object by the illumination light;
introducing, by a light introduction unit, the illumination light into the high refractive index layer; and
detecting, by the light detection unit, the detection target light.

DESCRIPTION OF REFERENCE NUMERALS 1 chemical sensor
2 substrate
3 low refractive index layer
4 high refractive index layer
5 chemical sensor module
6 light introduction unit
10 chemical detection apparatus
11 light source
21 light detection unit

The invention claimed is:
1. A chemical sensor, comprising:
a substrate;
a low refractive index layer that is laminated on the substrate and has a second refractive index smaller than a first refractive index, wherein the first refractive index is a refractive index of a detection target object;
a high refractive index layer in which illumination light propagates, wherein the high refractive index layer is laminated on the low refractive index layer, wherein the high refractive index layer has a third refractive index larger than the first refractive index, and wherein the high refractive index layer comprises a holding surface on which the detection target object is held,
wherein the holding surface has adsorption regions to which the detection target object is adsorbed and non-adsorption regions to which the detection target object is non-adsorbed, and
wherein an area of the adsorption regions increases along a direction in which the illumination light propagates; and a light detection unit that is provided on the substrate and is configured to detect detection target light generated from the detection target object by the illumination light.

2. The chemical sensor according to claim 1, wherein the adsorption regions are separated by the non-adsorption regions.

3. The chemical sensor according to claim 2, wherein the light detection unit comprises a plurality of light detection units, and the adsorption regions are opposed to the plurality of light detection units, respectively.

4. The chemical sensor according to claim 2, wherein the light detection unit comprises a plurality of light detection units, and the respective adsorption regions are opposed to the plurality of light detection units.

5. The chemical sensor according to claim 1, wherein the adsorption regions are regions of the holding surface to which hydrophilic processing is applied, and the non-adsorption regions are regions of the holding surface to which hydrophobic processing is applied.

6. The chemical sensor according to claim 1, wherein the adsorption regions are regions of the holding surface to which hydrophobic processing is applied, and the non-adsorption regions are regions of the holding surface to which hydrophilic processing is applied.

7. The chemical sensor according to claim 1, wherein the non-adsorption regions are covered by a coating film to which the detection target object is non-adsorbed, and wherein the adsorption regions are uncovered by the coating film.

8. The chemical sensor according to claim 7, wherein the coating film has light reflectivity.

9. The chemical sensor according to claim 1, further comprising
a color filter that is provided between the light detection unit and the low refractive index layer, and is configured to block wavelengths other than that of the detection target light.

10. The chemical sensor according to claim 1, further comprising
an on-chip lens that is provided between the light detection unit and the low refractive index layer, and is configured to collect the detection target light on the light detection unit.

11. The chemical sensor according to claim 3, further comprising
light blocking walls that are provided on the low refractive index layer and partition the low refractive index layer into areas opposed to the respective plurality of light detection units.

12. The chemical sensor according to claim 1, wherein the illumination light is excitation light, and the detection target light is fluorescent light.

13. A chemical sensor module, comprising:
a chemical sensor comprising:
a substrate;
a low refractive index layer that is laminated on the substrate and has a second refractive index smaller than a first refractive index, wherein the first refractive index is a refractive index of a detection target object;
a high refractive index layer in which illumination light propagates, wherein the high refractive index layer is laminated on the low refractive index layer, wherein the high refractive index layer has a third refractive index larger than the first refractive index, and wherein the high refractive index layer comprises a holding surface on which the detection target object is held,
wherein the holding surface has adsorption regions to which the detection target object is adsorbed and non-adsorption regions to which the detection target object is non-adsorbed, and
wherein an area of the adsorption regions increases along a direction in which the illumination light propagates; and
a light detection unit that is provided on the substrate and is configured to detect detection target light generated from the detection target object by the illumination light; and
a light introduction unit that is joined to the chemical sensor and is configured to introduce the illumination light into the high refractive index layer.

14. A chemical detection apparatus, comprising:
a chemical sensor module comprising:
a chemical sensor comprising:
a substrate;
a low refractive index layer that is laminated on the substrate and has a second refractive index smaller than a first refractive index, wherein the first refractive index is a refractive index of a detection target object;
a high refractive index layer in which illumination light propagates, wherein the high refractive index layer is laminated on the low refractive index layer, wherein the high refractive index layer has a third refractive index larger than the first refractive index, and wherein the high refractive index layer comprises a holding surface on which the detection target object is held,
wherein the holding surface has adsorption regions to which the detection target object is adsorbed and non-adsorption regions to which the detection target object is non-adsorbed, and
wherein an area of the adsorption regions increases along a direction in which the illumination light propagates; and
a light detection unit that is provided on the substrate and is configured to detect detection target light generated from the detection target object by the illumination light; and
a light introduction unit that is joined to the chemical sensor and is configured to introduce the illumination light into the high refractive index layer; and
a light source configured to apply the illumination light to the light introduction unit.

15. A chemical detection method, comprising:
preparing a chemical sensor comprising:
a substrate;
a low refractive index layer that is laminated on the substrate and has a second refractive index smaller than a first refractive index, wherein the first refractive index is a refractive index of a detection target object;
a high refractive index layer in which illumination light propagates, wherein the high refractive index layer is laminated on the low refractive index layer, wherein the high refractive index layer has a third refractive index larger than the first refractive index, and wherein the high refractive index layer comprises a holding surface on which the detection target object is held, wherein the holding surface has adsorption regions to which the detection target object is adsorbed and non-adsorption regions to which the detection target object is non-adsorbed, and wherein an area of the adsorption regions increases along a direction in which the illumination light propagates; and a light detection unit that is provided on the substrate and is configured to detect detection target light generated from the detection target object by the illumination light;

introducing, by a light introduction unit, the illumination light into the high refractive index layer; and detecting, by the light detection unit, the detection target light.

* * * * *